US007861821B2

(12) United States Patent
Connor

(10) Patent No.: US 7,861,821 B2
(45) Date of Patent: Jan. 4, 2011

(54) ACOUSTICALLY TRANSMISSIVE BLANKET SYSTEM

(76) Inventor: Robert A. Connor, 100 Third Ave. S., #304, Minneapolis, MN (US) 55401-2590

( * ) Notice: Subject to any disclaimer, the term of this patent is extended or adjusted under 35 U.S.C. 154(b) by 0 days.

(21) Appl. No.: 12/271,989

(22) Filed: Nov. 17, 2008

(65) Prior Publication Data

US 2009/0127020 A1 May 21, 2009

Related U.S. Application Data

(60) Provisional application No. 61/003,330, filed on Nov. 17, 2007.

(51) Int. Cl.
*A61M 21/02* (2006.01)
*H04R 1/34* (2006.01)

(52) U.S. Cl. ......................... 181/141; 601/47; 381/388; 600/28

(58) Field of Classification Search ................. 181/141; 5/904; 601/47; 381/388; 600/26, 27, 28
See application file for complete search history.

(56) References Cited

U.S. PATENT DOCUMENTS

| | | | | | |
|---|---|---|---|---|---|
| 4,969,867 | A | * | 11/1990 | Cohen | 600/28 |
| 4,972,533 | A | * | 11/1990 | Brown | 5/413 R |
| 5,313,678 | A | * | 5/1994 | Redewill | 5/639 |
| 5,479,667 | A | * | 1/1996 | Nelson et al. | 5/636 |
| 5,687,246 | A | * | 11/1997 | Lancon | 381/386 |
| 5,784,733 | A | * | 7/1998 | Rasamny et al. | 5/482 |
| 5,974,607 | A | * | 11/1999 | Smith | 5/636 |
| 6,021,208 | A | * | 2/2000 | Kin-Lung | 381/338 |
| 6,062,337 | A | * | 5/2000 | Zinserling | 181/129 |
| 6,142,963 | A | * | 11/2000 | Black et al. | 601/57 |
| 6,170,602 | B1 | * | 1/2001 | Mann | 181/141 |
| 6,704,958 | B2 | * | 3/2004 | Gohl | 5/639 |
| 6,763,532 | B2 | * | 7/2004 | Gardenier et al. | 4/541.1 |
| 7,130,440 | B2 | * | 10/2006 | Maekawa et al. | 381/389 |
| 2002/0120176 | A1 | * | 8/2002 | Coviello | 600/28 |
| 2005/0117766 | A1 | * | 6/2005 | Ito et al. | 381/333 |
| 2005/0117767 | A1 | * | 6/2005 | Ito et al. | 381/333 |
| 2006/0056650 | A1 | * | 3/2006 | Hofmann et al. | 381/338 |
| 2006/0251284 | A1 | * | 11/2006 | Wiener | 381/388 |
| 2007/0079444 | A1 | * | 4/2007 | Ward | 5/655 |
| 2007/0242835 | A1 | * | 10/2007 | Davis | 381/73.1 |

* cited by examiner

*Primary Examiner*—Jeffrey Donels
*Assistant Examiner*—Jeremy Luks
(74) *Attorney, Agent, or Firm*—Schwegman, Lundberg & Woosner, P.A.

(57) ABSTRACT

A blanket system, which can include a blanket, quilt, or similar bed-covering can include one or more localized sound-emitting areas, one or more separately-located sound-processing devices, and one or more acoustically transmissive communication channels coupled between the sound-processing devices and the sound-emitting areas. A control can be provided to adjust the sound characteristics provided at the sound-emitting areas. The system can be used to mask unwanted sounds.

16 Claims, 1 Drawing Sheet

ACOUSTICALLY TRANSMISSIVE BLANKET SYSTEM

CLAIM OF PRIORITY

This patent application claims the benefit of priority, under 35 U.S.C. Section 119(e), to Robert A. Connor's U.S. Provisional Patent Application Ser. No. 61/003,330, entitled "Tinnitus-masking blanket system with one or more sound-emitting area(s) located apart from the sound-processing source(s)," filed on Nov. 17, 2007.

BACKGROUND

People suffering from tinnitus can have a ringing in one or both ears that keeps them from getting to sleep.

OVERVIEW

A device that can create a sound pattern, such as at or near the frequency of the tinnitus ringing, can help mask the ringing. This can help a tinnitus sufferer get sleep.

One approach for sound masking could use sound-producing devices external to the bed. However, the present inventor has recognized that if a person with tinnitus wants to sleep with their head partially or fully covered by a blanket, then the blanket can muffle the masking sound, leaving the annoying tinnitus ringing remaining clear. Also, with a sound-producing device that is external to the bed, it is difficult to localize the masking sound near the head of the person with tinnitus. Thus, if there is another person sleeping in the same bed, or in the same room, this other person would be forced to hear the masking sound with a similar intensity as its intended recipient, and the masking sound may annoy the other person.

Another approach could use a sound-producing pillow. However, the present inventor has recognized that there can be a tradeoff that is difficult to resolve between (1) comfort (e.g., from greater padding between the sound source and the person's head pressing down on the pillow) and (2) sound muffling (e.g., by any greater padding between the sound source and the person's head pressing down on the pillow). Too much padding and the masking sound is muffled. Too little padding and the pillow is uncomfortable. The present inventor has recognized that padding is less of an issue for comfort for something covering the top of the head, such as a blanket, because the head is not pressing down on it. The present acoustically transmissive blanket system can allow a user full market choice in selecting a pillow, such as to obtain a desired characteristic such as relative padding or firmness.

Another approach could use a sound-producing device in a blanket, but without one or more acoustically transmissive communication channels to conduct acoustic energy from the sound-producing device to one or more separate sound-emitting areas. This approach has limitations. As an example of one limitation, sound-producing devices tend to have some rigid components. Having a rigid sound-producing device in a blanket pressing against a person's head or neck area can be uncomfortable and could distract that person from getting to sleep. In contrast, the flexible acoustically transmissive communication channels described in this document can be more comfortable for a sleeper to have embedded in a blanket that is pressed against the sleeper's head or neck. With an acoustically transmissive communication channel, a rigid sound-producing component of the system can be located away from the head and neck area.

An example of a second limitation of a sound-producing device without one or more acoustically transmissive communication channels is that it generally will emit sound from just one place. This can make it difficult to create broad sound-emitting areas across the blanket, such as to accommodate different sleeping postures during the night for one sleeper, or to enable sound allocation or distribution between different sleepers in the same bed. In contrast, acoustically transmissive communication channels can more conveniently be configured to create broad sound-emitting areas across the blanket, such as to accommodate different sleeping postures during the night for one sleeper, or enable sound allocation or distribution such as to help provide localized sound environments for different sleepers in the same bed.

Another approach could use a sound-producing device attached to the head or within the ear. However, the present inventor has recognized that some people can have difficulty getting used to wearing an attached or inserted device while sleeping. The present acoustically transmissive blanket system, on the other hand, need not require such attachment or insertion. The acoustically transmissive blanket system can provide a flexible and comfortable way to emit sound next to a sleeper's ear or ears. This can help mask tinnitus, such as for a person who wishes to have his or her head partially or fully covered by a blanket. The acoustically transmissive blanket system does not require a potentially difficult adjustment to wearing an attached or inserted device when sleeping.

The present acoustically transmissive blanket system can allow one or more sleepers to create one or more localized sound environments, such as to help promote sleep by masking an unwanted noise, such as ringing due to tinnitus. It can also be useful for masking one or more other types of unwanted noise such as snoring by another person. In an example, the present acoustically transmissive blanket system can include a blanket, one or more flexible and comfortable sound-emitting areas on the blanket, one or more sound-processing devices located apart from the sound-emitting areas, one or more acoustically transmissive channels between the sound-processing devices and sound-emitting areas, and one or more controls such as to adjust one or more characteristics of the sound. This blanket system can offer one or more advantages, such as in terms of the allowable range of head postures for which tinnitus masking is effective, or sleeping comfort as compared to certain other approaches.

Example 1 includes a blanket system comprising: a blanket that is sized and shaped to partially or fully cover a sleeping person, wherein some or all of the blanket comprises a sound-emitting area; and an acoustically transmissive communication channel, generally located in association with the blanket, that acoustically communicates acoustic energy from a sound-processing device to the sound-emitting area where this energy is emitted as sound.

Example 2 includes the blanket system of Example 1, in which the acoustically transmissive communication channel communicates acoustic energy through a gaseous, liquid, or other non-solid medium.

Example 3 includes the blanket system of Example 1, in which the acoustically transmissive communication channel includes a flexible tube comprising a lumen carrying a gaseous, liquid, or other non-solid medium.

Example 4 includes the blanket system of Example 3, wherein, outside of the sound-emitting area, the flexible tube is acoustically insulated, such that acoustic energy is not substantially emitted outside the sound-emitting area.

Example 5 includes the blanket system of Example 3, wherein the flexible tube comprises in the sound-emitting area of the blanket at least one of a tube wall hole or diaphragm 12 configured to emit acoustic energy in sound-emitting area.

Example 6 includes the blanket system of Example 5, wherein the flexible tube comprises, in the sound-emitting area, a hole 12 in the tube wall that is configured to allow direct movement of air out of the tube to emit acoustic energy from the tube.

Example 7 includes the blanket system of Example 5, wherein the flexible tube comprises, in the sound-emitting area, a diaphragm 12 in the tube wall, wherein the diaphragm is configured to retain a gaseous, liquid, or other non-solid medium within the flexible tube, but to allow movement of the diaphragm in response to acoustic energy communicated via the medium within the flexible tube to emit acoustic energy from the tube via the diaphragm.

Example 8 includes the blanket system of Example 1, comprising a sound-processing device wherein the sound-processing device communicates acoustic energy into the acoustically transmissive communication channel, which acoustically communicates the acoustic energy via the acoustically transmissive communication channel to the sound-emitting area, where at least a portion of the communicated acoustic energy is emitted as sound.

Example 9 includes the blanket system of Example 8, wherein the sound-processing device is configured to generate a source signal and to use the source signal to generate acoustic energy in correspondence with the source signal.

Example 10 includes the blanket system of Example 8, wherein the sound-processing device is configured to receive an input signal from another source, and to use the received input signal to generate acoustic energy in correspondence with the received input signal.

Example 11 includes the blanket system of Example 8, wherein the sound-processing device is configured to provide acoustic energy comprising at least one of a tone music or other sound pattern.

Example 12 includes the blanket system of Example 8, wherein the sound-processing device is configured to be located outside of and separate from the blanket.

Example 13 includes the blanket system of Example 8, wherein the sound-processing device is configured to be located inside of, or in close association with, the blanket, but separated from the sound-emitting area by the acoustically transmissive communication channel.

Example 14 includes the blanket system of Example 1, comprising a control, configured to adjust at least one characteristic of the sound emitted at the sound-emitting area.

Example 15 includes the blanket system of Example 14, wherein the control is configured to adjust at least one of a volume, a frequency, or a spatial sound output range, area, or pattern.

Example 16 includes the blanket system of Example 1, comprising a control, configured to differentially adjust a sound characteristic of first and second sound-emitting areas of the blanket, wherein the first and second sound-emitting areas are separated from each other by a region of the blanket that is not configured as a sound-emitting area.

Example 17 includes a method comprising: providing or obtaining a blanket that is sized and shaped to partially or fully cover a sleeping person, wherein some or all of the blanket comprises a sound-emitting area; acoustically communicating acoustic energy to the sound-emitting area via an acoustically transmissive channel that is generally located in association with the blanket; and emitting sound at the sound-emitting area in response to the acoustic energy communicated via the channel.

Example 18 includes the method of Example 17, wherein emitting sound at the sound-emitting area comprises emitting sound that substantially masks a tinnitus ringing of a user of the blanket.

Example 19 includes the method of Example 18, wherein emitting sound at the sound-emitting area comprises allowing airflow in or out of the acoustically transmissive channel at the sound-emitting area.

Example 20 includes the method of Example 17, wherein emitting sound at the sound-emitting area comprises vibrating a diaphragm 12 at the sound-emitting area in response to acoustic energy that is communicated to the sound-emitting area via a medium in the acoustically-transmissive channel.

This overview is intended to provide an overview of subject matter of the present patent application. It is not intended to provide an exclusive or exhaustive explanation of the invention. The detailed description is included to provide further information about the present patent application

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 2:
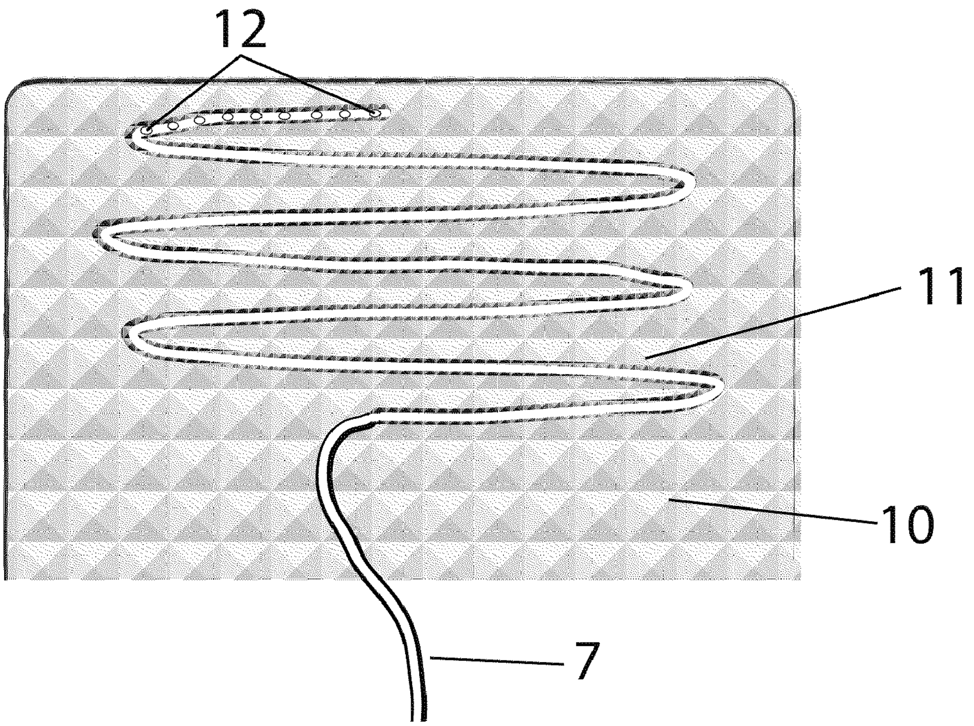
FIG. 2 shows an example of an acoustically transmissive channel from the sound-processing device to a sound-emitting area of the blanket system.
Figure 1:
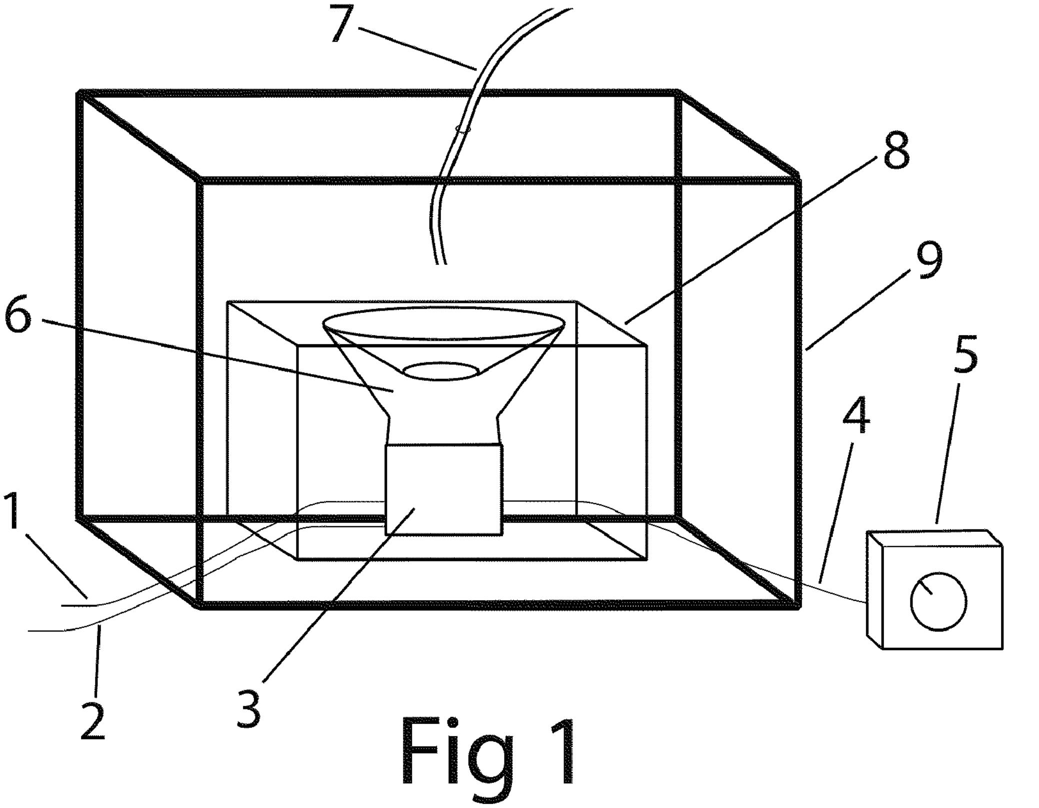
FIG. 1 shows an example of a sound-processing device that can be included as part of the present acoustically transmissive blanket system.

FIGS. 1 and 2 show an example of the present acoustically transmissive blanket system, such as in which the sound-processing device can include an enclosed speaker, such as in a sound-insulated box external to the blanket. The acoustically transmissive blanket system can include one or more acoustically transmissive channels. The acoustically transmissive channel can provide a flexible element that conducts the sound to the blanket area. The acoustically transmissive channel can be located within or in close association with the blanket. The acoustically transmissive communication channel can be configured to substantially confine acoustic energy being transmitted via the medium in the channel, such that the acoustic energy substantially does not leave the channel, except at one or more specified sound-emitted locations. In an example, the flexible element can include a flexible air-filled polymer tube from the box to the blanket. The tube can have a circular or other cross-sectional area, and can be embedded between upper and lower blanket layers, in an example. The sound-emitting area of the blanket can be embedded with flexible loops of the polymer tube, that can have one or more holes in the tube wall to emit sound. This is just one possible example of the present acoustically transmissive blanket system. FIG. 1 shows the sound-processing speaker in a box compartment and the starting segment of the flexible tubing. Only the three-dimensional box frames are shown in FIG. 1. This allows a conceptual view of the inner components, as if the box walls between the frames were transparent. In a practical example, the box walls can be solid planes, such as to provide sound insulation, and need not be transparent. FIG. 2 shows an example of the sound-emitting area of the blanket, such as with an ending segment of the flexible tubing embedded in the blanket. In this example, the upper fabric layer of the blanket is shown as transparent. This allows a conceptual view of the embedded tubing, but in a practical example, the upper fabric layer need not be transparent.

FIG. 1 shows an example of a sound-processing device that can be included as part of the present acoustically transmissive blanket system. In this example, the sound-processing device can receive electrical power, such as through a power line (1). In an example, the sound-processing device can receive an electromagnetic input sound signal, such as through a two-wire signal input line (2), such as from an external source, such as a CD player, MP3 player, noise generator, or the like. Many such external sound or music sources are possible.

In an example, the electromagnetic input sound signal can be amplified, such as by a signal amplifier (3). Many electromagnetic input signal amplifiers are possible. In an example, a sound-adjusting control unit (5) can be connected to the amplifier (3), such as by a line (4) that can include the capability of being above to adjust sound volume. Many volume adjusting methods, such as rotary potentiometers, are possible.

In an example, the electromagnetic sound signal amplified by amplifier (3) and adjusted by the control unit (5), can become the input signal for a sound-producing device, such as a cone speaker (6), which can transduce its electromagnetic input signal into sound waves in the air. Many such speakers are possible. For masking relatively high-frequency sounds, such as tinnitus ringing, the speaker can be relatively small. In an example, the speaker can include a 3.5 inch diameter dome tweeter (e.g., with an 8-ounce magnet, 1 inch diameter voice coil, 150 W power output, and frequency response that can be substantially flat over a frequency range of about 2,000 Hz to about 20,000 Hz.

In an example, the sound waves in the air generated by the speaker (6) can propagate into a hollow, flexible polymer tube (7). Many variations of hollow, flexible polymer tubing are possible. The interior lumen width and the wall thickness of the polymer tube can be varied, such as based on the desired frequency range of the sound to be conducted, in an example. In an example, the tubing can include or be formed of PVC (polyvinylchloride), such as with an interior lumen diameter of about 5 mm.

In an example, the speaker and amplifier can be housed in a box-like speaker cabinet (8). In this example, only the frame of the cabinet is shown, so that the speaker and amplifier can be viewed conceptually in this diagram, but in practice the walls of this cabinet can be solid and can be opaque. In an example, the cabinet can be made of ⅜ inch thick plywood panels with a 3.5 inch circular hole on the top panel, into which the top of the speaker cone can be mounted.

In an example, the speaker cabinet can be included in the exterior box (9) of the sound-processing device. Only the frame of the exterior box (9) is shown, in this example, so that the inner components may be viewed in this diagram, but in practice the walls of this box (9) can be solid and sound-insulated. In an example, the exterior box (9) can be insulated, such as to reduce sound being emitted directly from the sound-processing device. Sound conduction from the device to the blanket areas via the flexible tubing, rather than through the air surrounding the sound-producing device, can allow greater localized control of where the tinnitus-masking sound is heard. This can be particularly useful for blanket examples that can include more than one sound-emitting area, such as can be selectively controlled by more than one person sleeping in the bed. The example shown in this diagram shows only one sound-emitting area, for illustrative clarity. It may be useful to include sound insulation on the exterior box (9) of the sound-processing device. In an example, the exterior box can be made of ½ inch thick plywood panels with R-4 fiberglass insulation or fire-resistant rigid insulation.

FIG. 1 shows an example in which the flexible, hollow polymer tube (7) can extend through a close-fitting or sealing hole in the exterior box of the sound-processing device (9), from which the tube (7) can head toward the blanket. The continuation of the tube (7) is shown at the base of FIG. 2.

FIG. 2 shows an example of a sound-emitting area of the blanket system. In this example, the sound-emitting area can include one or more loops of the flexible tubing, such as with one or more holes in its walls. The tubing can be embedded between bottom and top layers of the blanket, in an example. Shown at the base of FIG. 2, the flexible hollow polymer tube (7) is a continuation of the tube (7) shown leaving the top of FIG. 1. In an example, the tube (7) can be sewn between two layers of a blanket (10), which blanket can include any of a blanket, bedsheet, quilt, sleeping bag, bed covering, quilt, bed covering, or the like. Many different types of blanket material are possible, including wool, cotton, polyester, other synthetics, or various blends. In an example, the blanket layers are lightweight polyester fleece.

Shown at the base on FIG. 2, in this example, the flexible tube (7) can be relatively straight, and can have no holes in its walls outside of the sound-emitting area (11) of the blanket (10), such as to help efficiently conduct sound through the tube (7) from the sound processing device (9) to the sound-emitting area (11) of the blanket (10). In an example, such as shown at the top portion of FIG. 2, the flexible tube (7) can loop, and can have one or more holes in its walls to emit the air-based sound waves that originated in the sound-processing device (9). In an example, the holes can be ⅜ inch in diameter and can be spaced 4 inches apart.

In an example, the top portion of the blanket (11), such as shown in FIG. 2, is a portion of the blanket that can be used to partially or fully cover the sleeper's head. This can allow the sound-emitting area to be very near to one or both of a sleeper's ears across a broad variety of head postures, such as can occur as a sleeper tosses or turns while sleeping. Also, since the sound-emitting area can be physically distant from the rigid components of the sound-processing device, the user need not have the distraction of contact with a rigid structure while trying to sleep. Further, since the weight of the person's head need not press against the sound-emitting elements in the present blanket system, there is no need to force the user to choose between having more padding for comfort vs. less padding for sound clarity, as would otherwise be the case if the sound-emitting elements were located in a pillow under a person's head.

ADDITIONAL NOTES

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown and described. However, the present inventors also contemplate examples in which only those elements shown and described are provided.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. A blanket system comprising:

a blanket that is sized and shaped to partially or fully cover a sleeping person, wherein some or all of the blanket comprises a sound-emitting area;

an acoustically transmissive communication channel, integrated with the blanket, wherein the acoustically transmissive communication channel includes a flexible tube comprising a lumen carrying a gaseous, liquid, or other non-solid medium that acoustically communicates acoustic energy from a sound-processing device to the sound-emitting area where this energy is emitted as sound, wherein the flexible tube is integrated with the blanket and has enough structural flexibility such that a portion of the blanket including at least a portion of the flexible tube can be pressed against a portion of the person's head or neck; and wherein the flexible tube comprises, in the sound-emitting area of the blanket a diaphragm in the tube wall, the diaphragm configured to emit acoustic energy in sound-emitting area, wherein the diaphragm is configured to retain a gaseous, liquid, or other non-solid medium within the flexible tube, but to allow movement of the diaphragm in response to acoustic energy communicated via the medium within the flexible tube to emit acoustic energy from the tube via the diaphragm.

2. The blanket system of claim 1, wherein the flexible tube is configured such as to emit sound that substantially masks a tinnitus ringing of the person using the blanket when the blanket is pressed against the portion of the person's head or neck.

3. The blanket system of claim 1, wherein the flexible tube includes flexible loops of polymer tube.

4. The blanket system of claim 1, wherein, outside of the sound-emitting area, the flexible tube is acoustically insulated, such that acoustic energy is not substantially emitted outside the sound-emitting area.

5. The blanket system of claim 1, comprising a sound-processing device, wherein the sound-processing device communicates acoustic energy into the acoustically transmissive communication channel, which acoustically communicates the acoustic energy via the acoustically transmissive communication channel to the sound-emitting area, where at least a portion of the communicated acoustic energy is emitted as sound.

6. The blanket system of claim 5, wherein the sound-processing device is configured to generate a source signal and to use the source signal to generate acoustic energy in correspondence with the source signal.

7. The blanket system of claim 5, wherein the sound-processing device is configured to receive an input signal from another source, and to use the received input signal to generate acoustic energy in correspondence with the received input signal.

8. The blanket system of claim 5, wherein the sound-processing device is configured to provide acoustic energy comprising at least one of a tone, music, or other sound pattern.

9. The blanket system of claim 5, wherein the sound-processing device is configured to be located outside of and separate from the blanket.

10. The blanket system of claim 5, wherein the sound-processing device is configured to be located inside of, or in close association with, the blanket, but separated from the sound-emitting area by the acoustically transmissive communication channel.

11. The blanket system of claim 1, comprising a control, configured to adjust at least one characteristic of the sound emitted at the sound-emitting area.

12. The blanket system of claim 11, wherein the control is configured to adjust at least one of a volume, a frequency, or a spatial sound output range, area, or pattern.

13. The blanket system of claim 1, comprising a control, configured to differentially adjust a sound characteristic of first and second sound-emitting areas of the blanket, wherein the first and second sound-emitting areas are separated from each other by a region of the blanket that is not configured as a sound-emitting area.

14. A method comprising:

providing or obtaining a blanket that is sized and shaped to partially or fully cover a sleeping person, wherein some or all of the blanket comprises a sound-emitting area;

acoustically communicating acoustic energy to the sound-emitting area via an acoustically transmissive channel that is integrated with the blanket, wherein the acoustically transmissive channel includes a flexible tube comprising a lumen carrying a gaseous, liquid, or other non-solid medium, wherein the flexible tube is integrated with the blanket and has enough structural flexibility such that a portion of the blanket including at least a portion of the flexible tube can be pressed against the portion of the person's head or neck; and emitting sound at the sound-emitting area in response to the acoustic energy communicated via the channel, wherein emitting sound at the sound-emitting area comprises vibrating a diaphragm at the sound-emitting area in response to acoustic energy that is communicated to the sound-emitting area via a medium in the acoustically-transmissive channel.

15. The method of claim 14, wherein emitting sound at the sound-emitting area comprises emitting sound that substantially masks a tinnitus ringing of the person using the blanket when the blanket is pressed against the portion of the person's head or neck.

16. The method of claim 14, wherein emitting sound at the sound-emitting area comprises allowing airflow in or out of the acoustically transmissive channel at the sound-emitting area.

* * * * *